United States Patent [19]

McMorrow

[11] 4,320,787
[45] Mar. 23, 1982

[54] BLOOD SEGMENT PROCESSOR

[76] Inventor: John J. McMorrow, 55 Florence Ave., Oyster Bay, N.Y. 11771

[21] Appl. No.: 128,852

[22] Filed: Mar. 10, 1980

Related U.S. Application Data

[63] Continuation-in-part of Ser. No. 78,050, Sep. 24, 1979, abandoned.

[51] Int. Cl.³ .............................................. B65B 3/04
[52] U.S. Cl. ..................................... 141/98; 128/767; 128/214 D; 141/114
[58] Field of Search ............. 30/123, 124; 128/214 D, 128/314, 321, 325, 329 R, 767; 141/19, 114, 98, 329, 330; 222/81, 83

[56] References Cited

U.S. PATENT DOCUMENTS

| | | | |
|---|---|---|---|
| 2,646,799 | 7/1953 | Jacoby | 128/314 |
| 2,896,619 | 7/1959 | Bellamy | 128/214 D |
| 3,648,702 | 3/1972 | Bean | 128/321 |

Primary Examiner—Frederick R. Schmidt
Attorney, Agent, or Firm—James P. Malone

[57] ABSTRACT

Scissor type device for releasing fluid from a segmented plastic tube into a container. A hinged member has first and second arms. A spur cutter is mounted on the first arm a predetermined distance from the hinge. The interior wall of the second arm is shaped to position the segmented tube so that it is cut by the cutter at a central point on the tubular member when the arms are squeezed together. A cam surface is positioned on one arm. The interior wall of the other arm is shaped so that the cam surface will squeeze the tube so that the contents of the tube may be squeezed out.

3 Claims, 4 Drawing Figures

BLOOD SEGMENT PROCESSOR

This Application is a continuation-in-part of my prior Application, Ser. No. 78,050, filed Sept. 24, 1979, of the same title now abandoned.

This invention relates to blood processing means and more particularly to disposable means for processing segmented plastic tubes containing blood.

BACKGROUND ART

In blood testing, blood is drawn from a patient or donor through a plastic tube into a storage bag, the tube being attached to the bag. The tube is then cut off about eight or ten inches from the bag and sealed along its length into several segments. The segmented tube is then folded up and taped or otherwise affixed to the side of the bag. The purpose of this is that when it is desired to make a blood test, for instance, for determining the type of blood, one of the tubular segments can be cut off and the blood contained in that segment used for the test without opening the sealed bag.

The conventional method for cutting off the segment and releasing the blood into a test tube is with the use of scissors. The segment is cut at each end with the scissors and drained into a test tube. This is generally sloppy operation and results in blood being spilled and the scissor having to be cleaned and/or sterilized.

My prior Application provides means for blood testing and provides a scissor type spur cutter.

THE INVENTION

The present invention is a scissor type device for releasing fluid from a segmented plastic tube into a container. The device has a cutter so that the plastic tube may be cut. The device also has a cam portion so that the tube may be squeezed to strip out the contents into a container.

OBJECTS OF THE INVENTION

Accordingly, a principal object of the invention is to provide new and improved means for removing blood from segmented plastic tubes.

Another object of the invention is to provide new and improved means for removing blood from segmented plastic tubes comprising a scissor type device having a cutter and a squeezing cam so that the segment may be cut at both ends or cut at one end and squeezed to strip out the contents.

Another object of the invention is to provide new and improved means to release fluid from a segmented plastic tube into a container comprising, a hinged member having first and second arms, a cutter mounted on the first arm a predetermined distance from the hinge, the interior wall of the second arm being shaped to position the segmented tube so that it is cut by the cutter at a central point on the tubular member, when the arms are squeezed together, whereby a segmented plastic tube containing fluid may be inserted in said hinged member and cut by the cutter to thereby release the fluid, a cam surface positioned on one arm, the interior wall of the other arm being shaped so that the cam surface will squeeze the tube so that the contents of the tube may be squeezed out. This "milking" action is particularly applicable when only the lower extremity of the segment is pierced. Since cells will settle to the lower portion of the segment leaving serum on top, it is possible to pierce the lower segment and "milk" only cells. For some testing, cells without serum is desireable.

BRIEF DESCRIPTION OF THE DRAWINGS

These and other objects of the invention will be apparent from the following specifications of which.

DISCLOSURE OF THE INVENTION

Figure 1:
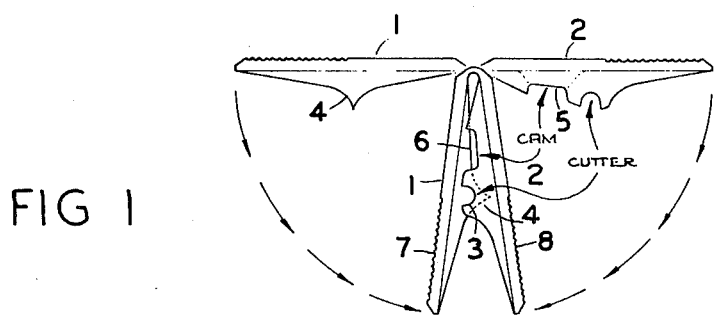
FIG. 1 is a plan view of an embodiment of the invention.

Referring to the figures, the invention comprises a scissor type device having two arms, 1 and 2, which are hinged together. The arm 2 has a U shaped cutter 3, which intersects with a pointed portion 4 on arm 1 when the scissor device is closed. As illustrated in FIG. 1, the arm 2 is slotted to receive the pointed portion 4 as illustrated by the dotted lines in FIG. 1. The arm 2 also has a cam surface 5 which co-acts with the portion 6 of arm 1, to squeeze a plastic tube. The device preferably has serrated finger grips 7 and 8 so that it can be conveninetly held between the thumb and forefinger of the user.

Figure 2:
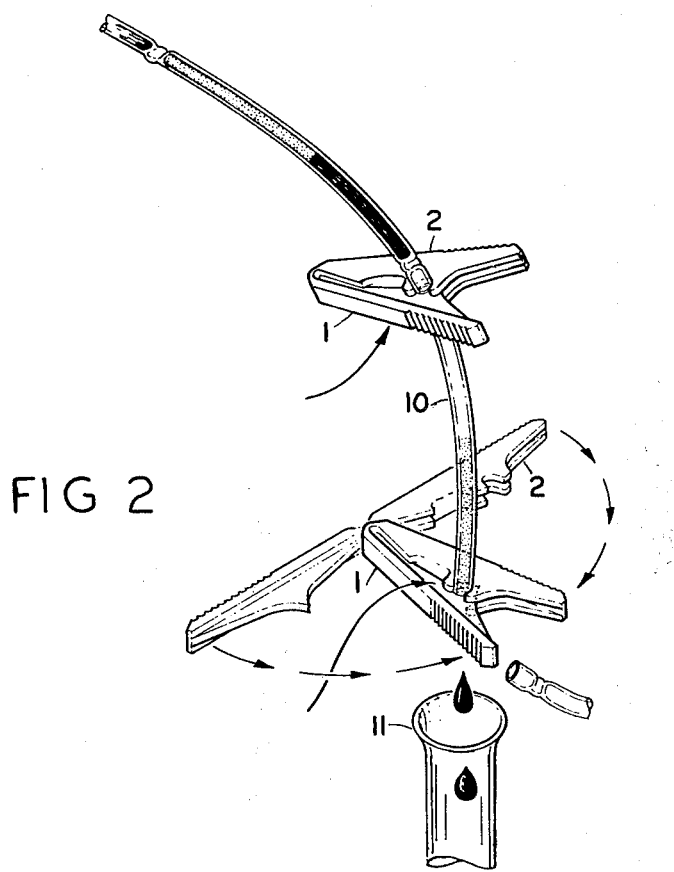
FIG. 2 is a diagram illustrating cutting both ends of the segment.

FIG. 2 illustrates one use of the invention in one mode of operation. The upper end of the tube segment 10 is punctured by the spur 4 on the arm 1. The lower end of the segment 10 is then cut off completely by the cutter so that the contents of th segment will drop freely into the container 11.

Figure 3:
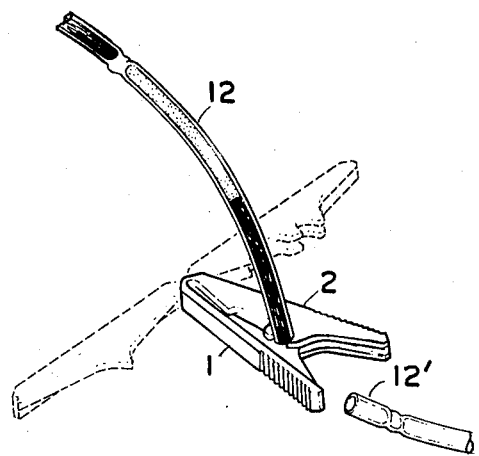
FIGS. 3 and 4 illustrate the alternate operation of cutting the lower end of the segment and squeezing the segment to strip out the contents into a container.
Figure 4:
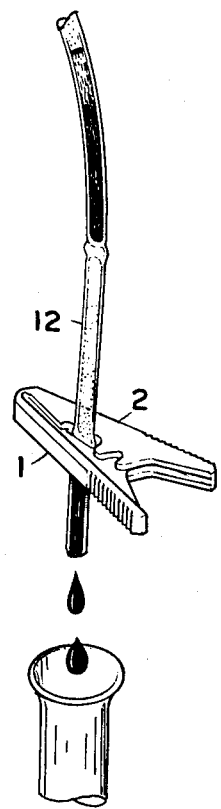

FIGS. 3 and 4 show another mode of operation in which the lower end 12' of the segment 12 is cut off and then the cam 5 portion of the device is placed around the upper portion of the segment squeezing and then slid down the segment 12 stripping out the contents into the container 13.

The scissor device of the present invention may be made of a one piece molded plastic member including the hinge portion. The device will not have to be sterilized since it is only used once and then disposed of.

It is claimed:

1. Means to release fluid from a segmented plastic tube into a container comprising:
   a hinged member having first and second arms,
   a cutter mounted on the first arm a predetermined distance from the hinge,
   the interior wall of the second arm being shaped to position the segmented tube so that it is cut by the cutter at a central point on the tubular member, when the arms are squeezed together,
   whereby a segmented plastic tube containing fluid may be inserted in said hinged member and cut by the cutter to thereby release the fluid,
   a cam surface positioned on one arm,
   the interior wall of the other arm being shaped so that the cam surface will squeeze the tube so that the contents of the tube may be squeezed out.

2. Apparatus as in claim 1 wherein the hinged member is a unitary molded plastic piece.

3. Apparatus as in claim 1 wherein the cutter is U shaped.